(12) United States Patent
Yuan et al.

(10) Patent No.: US 10,040,527 B2
(45) Date of Patent: Aug. 7, 2018

(54) LIFESAVING DEVICE AND LIFESAVING CONTROL METHOD

(71) Applicant: BOE TECHNOLOGY GROUP CO., LTD., Beijing (CN)

(72) Inventors: Zuo Yuan, Beijing (CN); Yifei Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/506,108

(22) PCT Filed: Aug. 22, 2016

(86) PCT No.: PCT/CN2016/096203
§ 371 (c)(1),
(2) Date: Feb. 23, 2017

(87) PCT Pub. No.: WO2017/118041
PCT Pub. Date: Jul. 13, 2017

(65) Prior Publication Data
US 2017/0313395 A1      Nov. 2, 2017

(30) Foreign Application Priority Data
Jan. 4, 2016    (CN) .......................... 2016 1 0006418

(51) Int. Cl.
*B63C 9/15*      (2006.01)
*A61B 5/00*      (2006.01)
(Continued)

(52) U.S. Cl.
CPC ............ *B63C 9/155* (2013.01); *A61B 5/0006* (2013.01); *A61B 5/02055* (2013.01); *B63C 9/13* (2013.01);
(Continued)

(58) Field of Classification Search
CPC .. B63C 9/00; B63C 9/08; B63C 9/081; B63C 9/125; B63C 9/20; B63C 11/02; B63C 11/04
(Continued)

(56) References Cited

U.S. PATENT DOCUMENTS 7,699,679 B2      4/2010  Lahyani
2005/0042956 A1   2/2005  Hodara
2009/0280705 A1   11/2009 Puls et al.

FOREIGN PATENT DOCUMENTS

CN        2294219 Y       10/1998
CN        101535120 A     9/2009
(Continued)

OTHER PUBLICATIONS

International Search Report of PCT/CN2016/096203 in Chinese, dated Oct. 18, 2016 with English translation.
(Continued)

*Primary Examiner* — Lars A Olson
(74) *Attorney, Agent, or Firm* — Collard & Roe, P.C.

(57) ABSTRACT

A lifesaving device and a lifesaving control method are provided. Wherein, the lifesaving device includes: at least one first detection module (200) configured for detecting human body biological characteristic information, a lifesaving device body (100) capable of being worn on a body of a user, and at least one first gasbag module (300) arranged on the lifesaving device body (100); after the first gasbag module (300) is activated, a lifesaving gasbag (1) can be popped up; the first detection module (200) is in signal connection with the first gasbag module (300) and is configured for activating the first gasbag module (300) when the biological characteristic information detected meets a first preset condition.

16 Claims, 6 Drawing Sheets

(51) Int. Cl.
*B63C 9/13* (2006.01)
*A61B 5/0205* (2006.01)
*B63C 9/18* (2006.01)
*B60C 29/00* (2006.01)
*B63C 9/00* (2006.01)

(52) U.S. Cl.
CPC .................. *B63C 9/18* (2013.01); *B63C 9/24* (2013.01); *B63C 2009/0023* (2013.01)

(58) Field of Classification Search
USPC ...................... 441/80, 88, 90, 91, 106; 2/2.5
See application file for complete search history.

(56) References Cited

FOREIGN PATENT DOCUMENTS

| CN | 101678883 A | 3/2010 |
|----|----|----|
| CN | 101853548 A | 10/2010 |
| CN | 201816732 U | 5/2011 |
| CN | 204021227 U | 12/2014 |
| CN | 204250330 U | 4/2015 |
| CN | 204368403 U | 6/2015 |
| CN | 204432997 U | 7/2015 |
| CN | 204489151 U | 7/2015 |
| CN | 204527583 U | 8/2015 |
| CN | 105416530 A | 3/2016 |
| CN | 205381377 U | 7/2016 |
| KR | 10-2014-0001001 A | 1/2014 |

OTHER PUBLICATIONS

Notice of Transmittal of the International Search Report of PCT/CN2016/096203 in Chinese, dated Oct. 18, 2016.
Written Opinion of the International Searching Authority of PCT/CN2016/096203 in Chinese, dated Oct. 18, 2016 with English translation.
Chinese Office Action in Chinese Application No. 201610006418.2, dated Jan. 26, 2017 with English translation.

LIFESAVING DEVICE AND LIFESAVING CONTROL METHOD

CROSS REFERENCE TO RELATED APPLICATIONS

This application is the National Stage of PCT/CN2016/096203 filed on Aug. 22, 2016, which claims priority under 35 U.S.C. § 119 of Chinese Patent Application No. 201610006418.2 filed on Jan. 4, 2016, the entire disclosures of which are incorporated herein by reference.

TECHNICAL FIELD

Embodiments of the present disclosure relate to a field of wearable technology, and in particular, to a lifesaving device and a lifesaving control method.

BACKGROUND

According to data in "Global Drowning Report: Preventing a Main Killer" of World Health Organization in 2014, drowning is one of top ten main death causes of children and youths in various regions. In total, 372,000 people are died of drowning every year, of which more than half of the people died of drowning are less than 25 years old.

A lifesaving device in a related art needs to be actively opened by a user. Obviously, after the user loses consciousness because of drowning, the lifesaving device cannot be made to work, and thus there is danger, which urgently needs to be solved.

SUMMARY

An objective of the present disclosure is to provide a technical solution according to which a lifesaving gasbag can also be opened after a user loses consciousness.

In order to achieve the above objective of the present disclosure, in one aspect, an embodiment of the present disclosure provides a lifesaving device, comprising:

At least one first detection module configured for detecting human body biological characteristic information;

A lifesaving device body capable of being worn on a body of a user; and

At least one first gasbag module arranged on the lifesaving device body; wherein, after being activated, the first gasbag module is capable of poping up a lifesaving gasbag;

The first detection module is in signal connection with the first gasbag module and is configured for activating the first gasbag module when the biological characteristic information detected meets a first preset condition.

Wherein, the first detection module is one or more of a heart rate sensor, a blood pressure sensor and a respiration sensor.

Optionally, the lifesaving device further comprises:

At least one second detection module arranged on the lifesaving device body and configured for detecting water pressure information; and And at least one second gasbag module arranged on the lifesaving device body;

The second detection module is in signal connection with the second gasbag module and is configured for activating the second gasbag module to pop up a lifesaving gasbag when the water pressure information detected meets a second preset condition.

Optionally, the first gasbag module is arranged at a position of the lifesaving device body corresponding to a chest of the user, and the second gasbag module is arranged at a position of the lifesaving device body corresponding to a back of the user.

Optionally, a number of the first gasbag module is one, and a number of the second gasbag modules is two.

Optionally, each lifesaving gasbag module includes:

A lifesaving gasbag, a gas generator and a power circuit;

Wherein, the power circuit is controlled by a sensor corresponding to the gasbag module to supply power to the gas generator, and after the power is supplied to the gas generator, the lifesaving gasbag is inflated.

Optionally, each gasbag module further includes:

A housing with a gasbag opening, and the lifesaving gasbag, the gas generator and the power circuit are respectively arranged in the housing;

After being inflated, the lifesaving gasbag can expand from a position of the gasbag opening to an exterior of the housing.

Optionally, each gasbag module includes:

A cover plate sealing and covering the gasbag opening through a buckle; wherein, a side of the cover plate is fixed to the exterior of the housing through a rotating shaft;

Wherein, after being inflated, the lifesaving gasbag is capable of eject open the cover plate sealing and covering the gasbag opening from an interior of the housing.

Optionally, each gasbag module further includes:

A dye source configured for positioning in water;

Wherein, after the lifesaving gasbag opens the cover plate sealing and covering the gasbag opening from the interior of the housing, dye in the dye source is diffused after encountering water.

Optionally, each gasbag module further includes:

A manual switch configured for controlling the power circuit to supply power to the gas generator, wherein, the above manual switch is arranged on the exterior of the housing.

Optionally, a buffering layer is arranged on the exterior of the housing of each gasbag module.

Optionally, the housing of each gasbag module is further provided with a thread structure for being detachably fixed to the lifesaving device body.

In another aspect, the present disclosure further provides a lifesaving control method applied to the above lifesaving device, comprising:

Detecting human body biological characteristic information of a user;

Activating a first gasbag module to pop up a lifesaving gasbag if the human body biological characteristic information meets a first preset condition.

Optionally, when the lifesaving device comprises a second detection module and a second gasbag module, and a first gasbag module is arranged at a position of a lifesaving device body corresponding to a chest of the user, and the second gasbag module is arranged at a position of the lifesaving device body corresponding to a back of the user, the control method comprises:

Detecting water pressure information after the first gasbag module pops up the lifesaving gasbag;

Activating the second gasbag module to pop up a lifesaving gasbag if the water pressure information meets a second preset condition.

The technical solution of the present disclosure has following advantages:

The lifesaving device and the control method of the present disclosure can detect the human body biological information of the user in real time, and it can be judged whether the user is in a drowning state or not according to the human body biological information, so as to actively activate the lifesaving gasbag module to work, and avoid an accident that the user cannot open the lifesaving gasbag by himself/herself when the user loses consciousness.

DETAILED DESCRIPTION

In order to make technical problems, technical solutions and advantages of the present disclosure more apparent, detailed description will be performed hereinafter in connection with the drawings and the specific embodiments.

The present disclosure provides a solution with respect to a problem that a lifesaving gasbag of a lifesaving device in the related art cannot be opened when a user loses consciousness.

Figure 1:
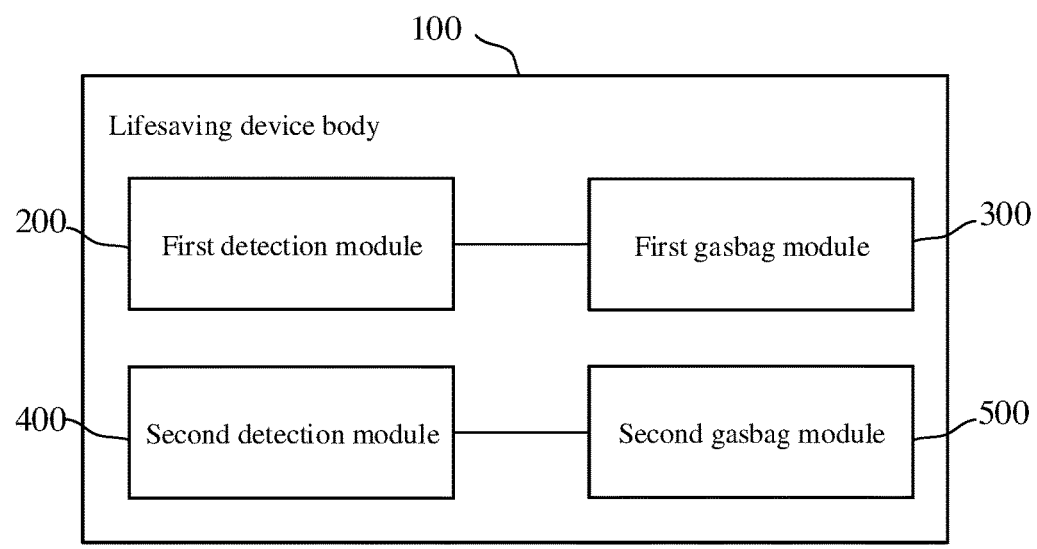
FIG. 1 is a structural schematic diagram of a lifesaving device of the present disclosure.

In one aspect, some embodiments of the present disclosure provide a lifesaving device, as shown in FIG. 1, comprising:

A lifesaving device body 100 capable of being worn on a body of a user;

At least one first detection module 200 for detecting human body biological characteristic information, and the first detection module 200 can be, but not limited to, arranged on the lifesaving device body 100; and At least one first gasbag module 300 arranged on the lifesaving device body;

Wherein, the first detection module 200 is in signal connection (which can be signal connection of a wired manner or signal connection of a wireless manner) with the first gasbag module 300, and is configured for activating the first gasbag module 300 to work when the biological characteristic information detected meets a first preset condition.

The lifesaving devices in some embodiments of the present disclosure can detect the human body biological information of the user in real time, and it can be judged whether the user is in a drowning state or not according to the human body biological information, so as to actively activate a lifesaving gasbag module, and avoid an accident that the user cannot open a lifesaving gasbag by himself/herself when the user loses consciousness.

As an exemplary introduction, in a specific implementation process, the first detection module of the present disclosure can be one or more of a heart rate sensor, a respiration sensor or a blood pressure sensor in the related art; by detecting a heart rate, blood pressure and respiration of the user, it is determined whether the user is in the drowning state or not, and then it is decided whether the first gasbag module to be activated or not.

For example, when the user falls into water and is in the drowning state, an electrocardiogram ECG signal, a pulse wave PPG signal and related indexes obviously change compared with numerical values in a normal state; after the first detection module of the present disclosure detects an abnormity, the first gasbag module can be activated in time, so as to avoid that danger happens to the user. In addition, based on the principle, with respect to a case that a user being able to swim can keep afloat by himself/herself after falling into water, the first detection module can also determine that the user is not in the drowning state according to numerical values of a normal electrocardiogram ECG signal and a normal pulse wave PPG signal, so as to avoid that the first gasbag module is opened mistakenly.

In addition, the present disclosure also can judge whether the user is in the drowning state or not according to a depth at which the user sinks in water. That is, as shown in FIG. 1, the lifesaving device in some embodiments of the present disclosure further comprises:

At least one second detection module 400 for detecting water pressure information; and the second detection module 400 can be, but not limited to, arranged on the lifesaving device body 100;

At least one second gasbag module 500 arranged on the lifesaving device body;

Wherein, the second detection module 400 is in signal connection (which can be signal connection of a wired manner or signal connection of a wireless manner) with the second gasbag module 500 and is configured for activating the second gasbag module to work when the water pressure information detected meets a second preset condition.

In actual application, a water pressure value corresponding to a dangerous warding depth can serve as the second preset condition; when the water pressure information detected by the second detection module is greater than the second preset condition, it is determined that drowning danger happens to the user, and the second gasbag module is activated in time, so that the user can emerge from the water as soon as possible.

It is explained herein that, the lifesaving device of some embodiments of the present disclosure can help the user to turn on the lifesaving device when the user loses consciousness. Of course, as a preferred solution, the solution of the present disclosure can be that the user actively opens the first gasbag module and the second gasbag module, and therefore protection can be provided more timely.

The lifesaving gasbag module of the present disclosure is introduced in detail hereinafter in connection with a specific implementation mode.

Figure 2A:
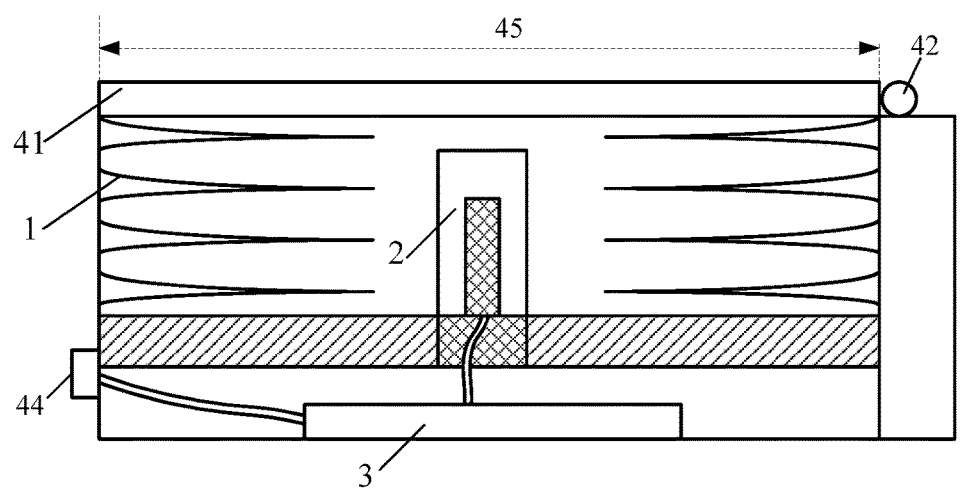
FIGS. 2a, 2b and 3 are structural schematic diagrams of a first gasbag module of the present disclosure.
Figure 2B:
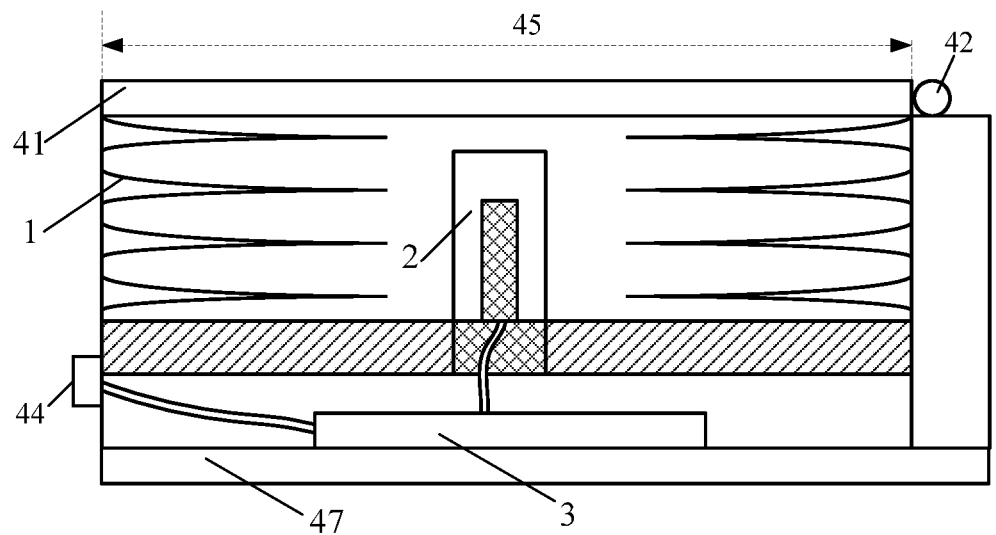
Figure 3:
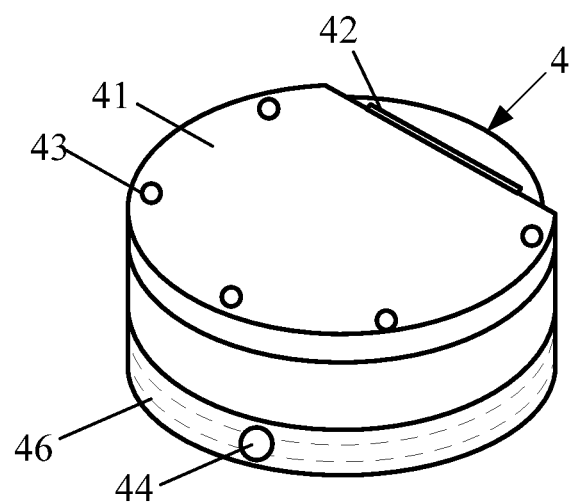

Structures of the first gasbag module and the second gasbag module of the present disclosure are similar, it will be illustrated hereinafter with the first gasbag module as an example, and as shown in FIGS. 2a, 2b and 3, the first gasbag module includes:

A lifesaving gasbag 1, a gas generator 2 and a power circuit 3;

Wherein, the power circuit of the first gasbag module is controlled by the first detection module to supply power to the gas generator of the first gasbag module; the power circuit of the second gasbag module is controlled by the second detection module to supply power to the gas generator of the second gasbag module; and after the power is supplied to the gas generator similarly, the corresponding lifesaving gasbag can be inflated.

In actual application, the gas generator in some embodiments of the present disclosure can be a boosting type gas generator, and after the boosting type gas generator is powered on, an explosion happens, lots of gas is generated; Or, the gas generator in some embodiments of the present disclosure can be a gas storage type gas generator, the gas storage type gas generator is composed of a gas storage tank, and after the gas storage type gas generator is powered on, the gas storage tank can release lots of gas.

Specifically, the first gasbag module further includes:

A housing 4 with a gasbag opening 45, and the lifesaving gasbag 1, the gas generator 2 and the power circuit 3 are respectively arranged in the housing 4. After being inflated, the lifesaving gasbag is capable of expanding from a position of the gasbag opening 45 to an exterior of the housing 4.

Further, in some embodiments of the present disclosure, the housing further respectively includes a cover plate 41, the cover plate 41 can seal and cover the gasbag opening 45 through a buckle 43, and one side of the cover plate is fixed to the exterior of the housing 4 through a rotating shaft 42. After being inflated, the lifesaving gasbag 1 is capable of opening the cover plate 41 sealing and covering the gasbag opening 45 from an interior of the housing 4.

In addition, in order to facilitate rescue workers to find the drowning user, the first gasbag module and the second gasbag module further respectively include: a dye source configured for positioning, in water. After the lifesaving gasbag 1 opens the cover plate 41 sealing and covering the gasbag opening 45 from the interior of the housing 4, dye in the dye source can be diffused after encountering water, and the rescue workers trace the person falling into water according to the dye in water. Of course, as a preferred solution, in order to prevent water source pollution, the dye in the dye source in the implementation manner is decomposable dye, such as aromatic amine.

In addition, on the exterior of the housing 4 of the first gasbag module, a manual switch 44 for controlling the power circuit 3 to supply power to the gas generator 2 is further arranged. After the user falls into water, the gas generator can be automatically controlled to inflate the lifesaving gasbag 1 before the user loses consciousness.

In addition, the housing of the first gasbag module is further provided with a buffering layer 47 which can reduce a part of impacting force applied to the body of the user in a process that the lifesaving gasbag expands fast. In some embodiments of the present disclosure, the buffering layer 47 can be arranged as shown in FIG. 2*b*.

In addition, as a preferred solution, in order to facilitate that the user can conveniently replace the used lifesaving gasbag, the first gasbag module and the second gasbag module of the present disclosure are detachably fixed to the lifesaving device body. In order to achieve the solution, as shown in FIG. 3, the housing of the first gasbag module and the second gasbag module is provided with a thread structure 46 and is fixed to the lifesaving device body through the thread structure 46.

Actual application of the lifesaving device of the present disclosure is exemplarily introduced hereinafter.

Figure 4:
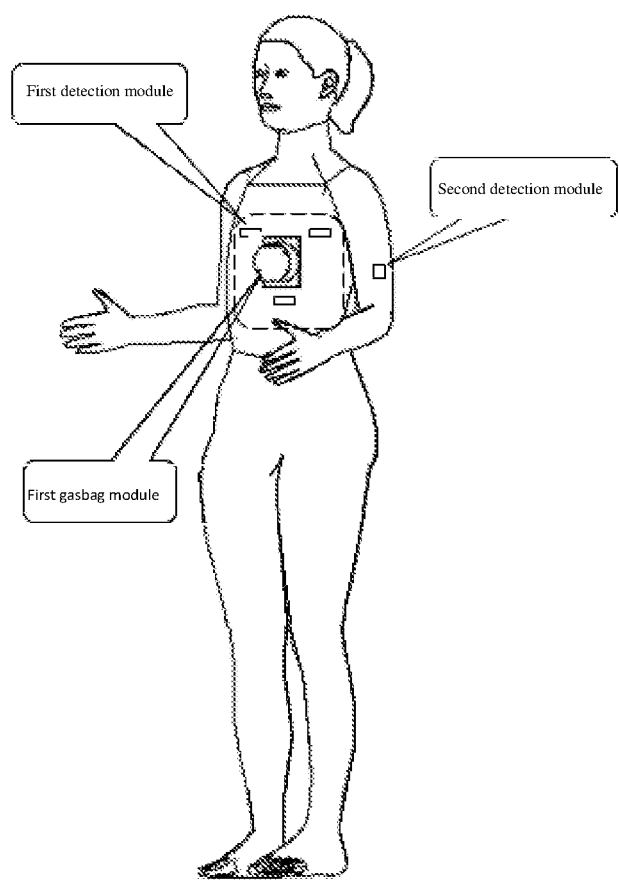
FIGS. 4 and 5 are structural schematic diagrams when a user wears the lifesaving device of the present disclosure.
Figure 5:
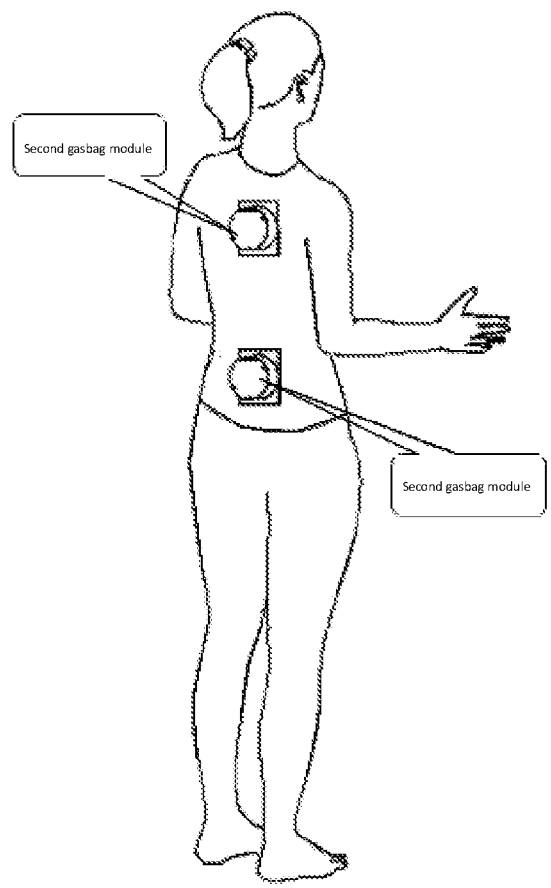

As shown in FIGS. 4 and 5, the lifesaving device body in some embodiments of the present disclosure is a life jacket (of course, as other feasible solutions, the lifesaving device body can also be a banding, a knapsack, a bracelet and the like which will not be repeatedly described herein).

Wherein, the number of the first gasbag module is one, it is arranged at a position of the lifesaving device body corresponding to the chest of the user; the number of the second gasbag modules is two, they are arranged at a position of the lifesaving device body corresponding to the back of the user.

Specifically, in an actual application, the first detection module and the second detection module can be arranged on the lifesaving device body just like the first detection module and the second detection module; or, the first detection module and the second detection module can also serve as other independent wearable devices, such as a bracelet, a finger ring and the like, to be worn on the body of the user.

Figure 6:
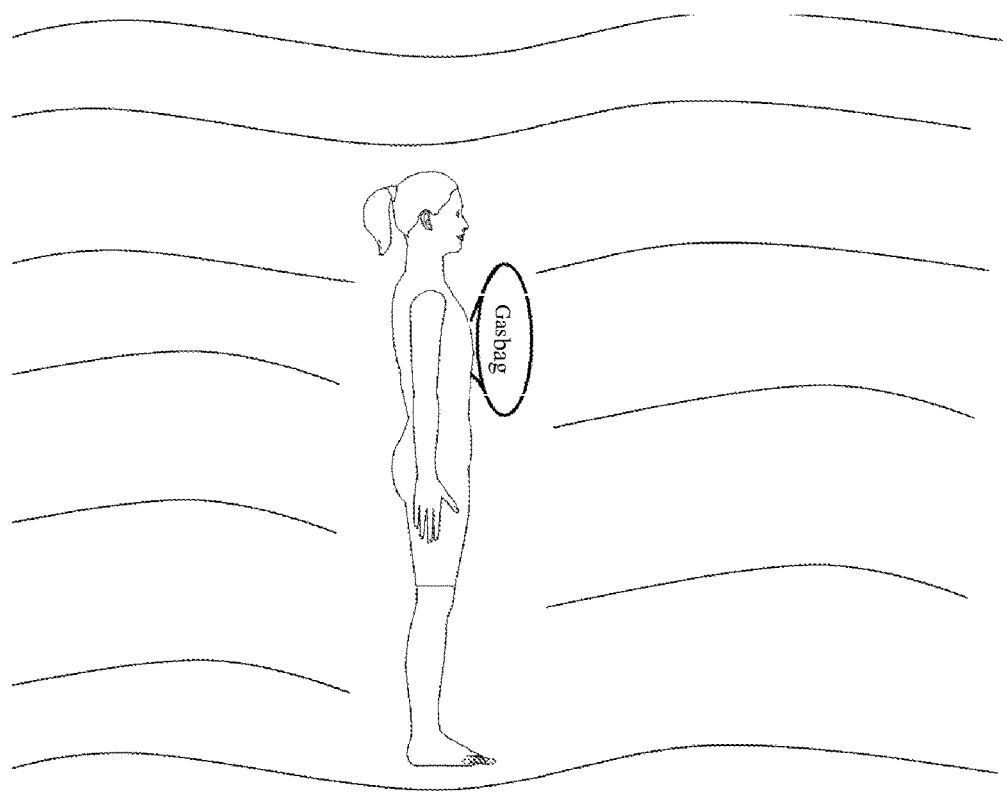
FIGS. 6 to 8 are schematic diagrams when the lifesaving device of the present disclosure floats in water to float up the user.
Figure 7:
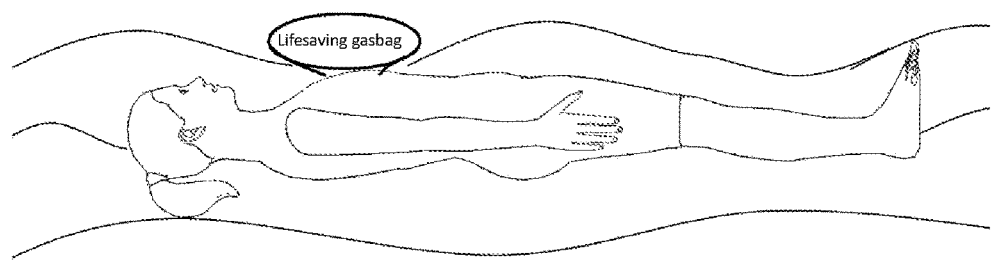
Figure 8:
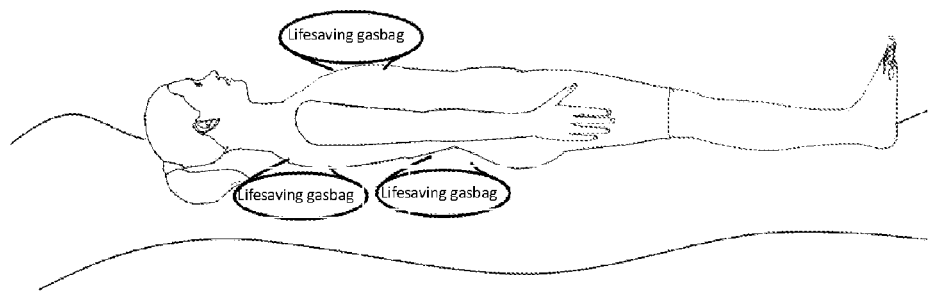

After the user falls into water, as shown in FIG. 6, the first gasbag module at the position of the chest firstly open the lifesaving gasbag, so that the user can float up at a vertical angle till the user is kept on a water surface with a posture as shown in FIG. 7. Then, the second gasbag module at the position of the back further opens the lifesaving gasbag to make the face of the user emerges from water. FIG. 8 is not relevantly explained.

It can be seen that, in actual application, the lifesaving device of the present disclosure can actively open the lifesaving gasbag under a state that the user loses consciousness and can further make the face of the user completely emerge out of the water, the user is prevented from asphyxia, and therefore quite high safety is achieved.

Herein, what needs to be explained is that, the above actual application is only used for exemplarily introducing the lifesaving device of the present disclosure, the number of the first gasbag module and the number of the second gasbag module are not limited; and the position of the first gasbag module arranged on the lifesaving device body and the position of the second gasbag module arranged on the lifesaving device body are not limited. On a premise of not apart from the principle of the present disclosure, other implementation modes are not repeatedly described by giving an example herein.

Correspondingly, the present disclosure further provides a lifesaving control method applied to the above lifesaving device, comprising:

Step 1: detecting human body biological characteristic information of a user;

Wherein, the above human body biological characteristic information can reflect a drowning state of the user; it can be respiration, heart rate, blood pressure and the like of the user.

Step 2: activating the first gasbag module to work if the human body biological characteristic information meets a first preset condition.

In the step, a numerical value of the human body biological characteristic information after drowning serves as a judgment threshold, and when detected human body biological characteristic information is lower than or reaches the threshold, it is determined that the first preset condition is met.

The control method of the embodiment can detect the human body biological information of the user in real time, and it can be judged whether the user is in the drowning state or not according to the human body biological information, so as to actively activate the lifesaving gasbag module to work, and avoid an accident that the user cannot open the lifesaving gasbag by himself/herself when the user loses consciousness.

Further, when the lifesaving device comprises the second detection module and the second gasbag module, the first gasbag module is arranged at the position of the lifesaving device body corresponding to the chest of the user, and the second gasbag module is arranged at the position of the lifesaving device body corresponding to the back of the user, the control method in some embodiments of the present disclosure can further comprises:

Step 3: detecting water pressure information after the first gasbag module pops up the lifesaving gasbag;

Step 4: activate the second gasbag module to work if the water pressure information meets a second preset condition.

A control method of the present disclosure is introduced in an embodiment hereinafter.

Figure 9:
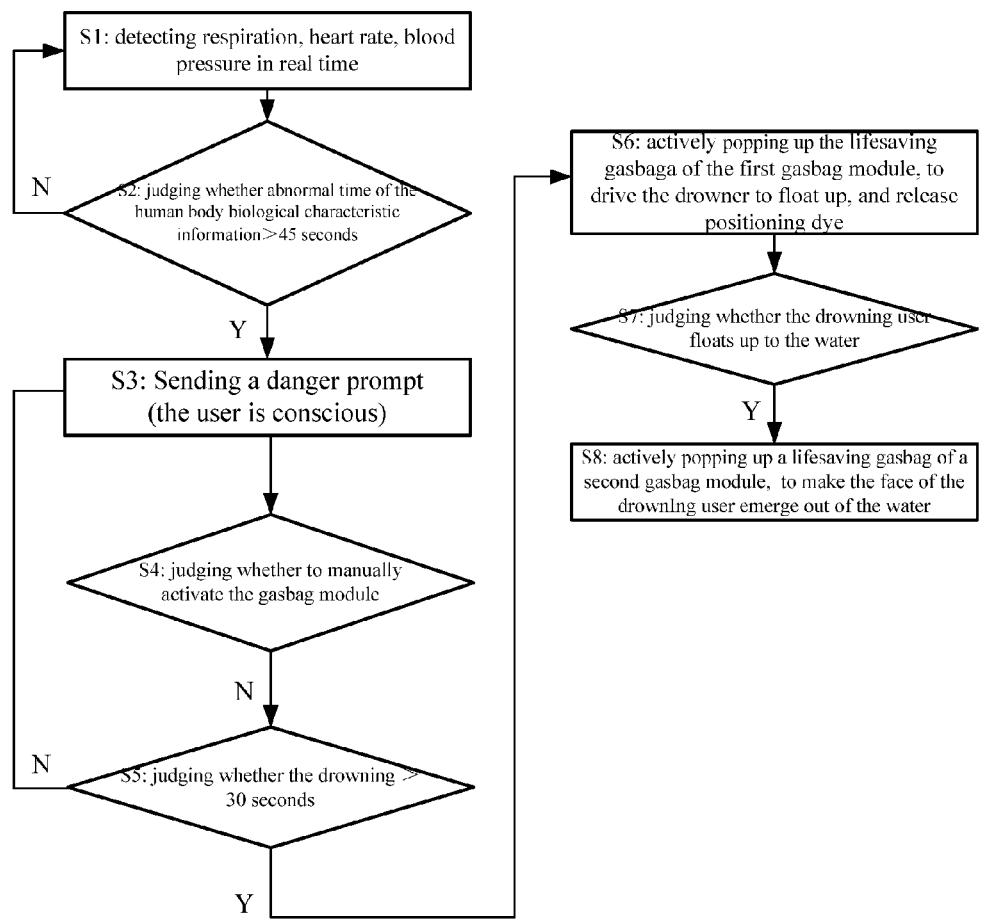
FIG. 9 is a flow diagram of a lifesaving control method of the present disclosure.

As shown in FIG. 9, the lifesaving control method of the present disclosure comprises steps of:

S1: detecting respiration, heart rate, blood pressure and other human body biological characteristic information of a user in real time. S2: judging whether abnormal time of the human body biological characteristic information exceeds a preset threshold or not; if yes, the human body may be submerged, executing step S3, and if not, continuing to execute step S1.

In the step, when the user is just drowned, the user will hold his/her breath temporarily and struggle up and down across the water, and therefore abnormal symptoms of stop of breathing, tachycardia, blood pressure increment and the like occur, and when this situation exceeds 45 seconds, it can be determined that the user is in a drowning state.

S3: sending a danger prompt, so that the drowning user can manually trigger a gasbag module in time.

S4: if the drowning user is conscious at the moment, selecting to manually trigger the gasbag module of a lifesaving device; if the drowning user loses consciousness and the gasbag module of the lifesaving device is not triggered in time, executing step S5.

S5: if corresponding symptoms of breathing weakening, blood pressure increment and changes of heartbeat from fast to slow happen to the drowning user because of drowning, judging whether the situation exceeds 30 seconds or not, if yes, executing step S6d, and if not, executing step S3.

S6: actively activating a first gasbag module to pop up a lifesaving gasbag.

After the first gasbag module is activated and a gas generator is powered up, a sharp reaction happens to an internal substance, lots of gas is generated, so that the lifesaving gasbag can fast expand, a top cover is open from the interior of a housing, and therefore the lifesaving gasbag can be totally expanded, and the human body is driven to float up at a vertical posture as shown in FIG. 6. Because buoyancy comes from the lifesaving gasbag of a chest, when the lifesaving gasbag of the chest emerges from the water, the user can float on the water with a face-upwards posture as shown in FIG. 7.

S7: judging whether the drowning user floats up to the water or not by detecting water pressure, if yes, executing step S8.

S8: activating a second gasbag module of a back to pop up a lifesaving gasbag to make a face of the drowning user emerge out of the water and guarantee that a mouth and a nose are not sunken in water.

The above mentioned are preferred embodiments of the present disclosure, what should be pointed out is that, for those skilled in the art, various changes and improvements may be made without departing from the spirit of the present disclosure, and the changes and improvements should also be considered within the scope of the claims of the disclosure.

The invention claimed is:

1. A lifesaving device, comprising:
at least one first detection module configured for detecting human body biological characteristic information;
a lifesaving device body capable of being worn on a body of a user;
at least one first gasbag module arranged on the lifesaving device body, wherein, after being activated, the first gasbag module is capable of popping up a first lifesaving gasbag;
the first detection module is in signal connection with the first gasbag module and is configured for activating the first gasbag module when the biological characteristic information detected meets a first preset condition,
at least one second detection module configured for detecting water pressure information; and
at least one second gasbag module arranged on the lifesaving device body, wherein, after being activated, the second gasbag module is capable of popping up a second lifesaving gasbag;
the second detection module being in signal connection with the second gasbag module and is configured for activating the second gasbag module when the water pressure information detected meets a second preset condition,
wherein, the first gasbag module and the second gasbag module are not in communication with each other.

2. The lifesaving device according to claim 1, wherein, the first detection module is one or more of a heart rate sensor, a blood pressure sensor and a respiration sensor.

3. The lifesaving device according to claim 1, wherein, the first gasbag module is arranged at a position of the lifesaving device body corresponding to a chest of the user, and the second gasbag module is arranged at a position of the lifesaving device body corresponding to a back of the user.

4. The lifesaving device according to claim 3, further comprising:
a number of the first gasbag module is one, and a number of the second gasbag modules is two.

5. The lifesaving device according to claim 1, wherein, each of the first gasbag module and the second gasbag module further includes:
a gas generator and a power circuit;
wherein, the power circuit is controlled by a sensor corresponding to the gasbag module to supply power to the gas generator, and after the power is supplied to the gas generator, the lifesaving gasbag is inflated.

6. The lifesaving device according to claim 5, wherein, the gas generator is at least one of a boosting type gas generator and a gas storage type gas generator.

7. A lifesaving device, comprising:
at least one first detection module configured for detecting human body biological characteristic information;
a lifesaving device body capable of being worn on a body of a user; and
at least one first gasbag module arranged on the lifesaving device body, wherein, after being activated, the first gasbag module is capable of popping up a lifesaving gasbag;
the first detection module is in signal connection with the first gasbag module and is configured for activating the first gasbag module when the biological characteristic information detected meets a first preset condition,
wherein, each of the first gasbag module and a second gasbag module includes: a lifesaving gasbag, a gas generator and a power circuit; wherein, the power circuit is controlled by a sensor corresponding to the gasbag module to supply power to the gas generator, and after the power is supplied to the gas generator, the lifesaving gasbag is inflated,
wherein,
each of the first gasbag module and the second gasbag module includes:
a housing with a gasbag opening, wherein, the lifesaving gasbag, the gas generator and the power circuit are respectively arranged in the housing;

after being inflated, the lifesaving gasbag can expand from a position of the gasbag opening to an exterior of the housing.

8. The lifesaving device according to claim 7, wherein, each of the first gasbag module and the second gasbag module further includes:
a cover plate sealing and covering the gasbag opening through a buckle, wherein, a side of the cover plate is fixed to the exterior of the housing through a rotating shaft;
wherein, after being inflated, the lifesaving gasbag is capable of opening the cover plate sealing and covering the gasbag opening from an interior of the housing.

9. The lifesaving device according to claim 8, wherein, each of the first gasbag module and the second gasbag module further includes:
a dye source configured for positioning in water;
wherein, after the lifesaving gasbag opens the cover plate sealing and covering the gasbag opening from the interior of the housing, dye in the dye source is diffused after encountering water.

10. The lifesaving device according to claim 9, wherein, the dye in the dye source is decomposable dye.

11. The lifesaving device according to claim 7, wherein, each of the first gasbag module and the second gasbag module further includes:
a manual switch configured for controlling the power circuit to supply power to the gas generator, wherein, the manual switch is arranged on the exterior of the housing.

12. The lifesaving device according to claim 7, wherein, a buffering layer is arranged on the exterior of the housing of each of the first gasbag module and the second gasbag module.

13. The lifesaving device according to claim 7, wherein, the housing of each of the first gasbag module and the second gasbag module is further provided with a thread structure for being detachably fixed to the lifesaving device body.

14. A lifesaving control method, applied to a lifesaving device according to claim 1, comprising:
detecting human body biological characteristic information of a user;
activating the first gasbag module to pop up the first lifesaving gasbag if the human body biological characteristic information meets a first preset condition.

15. The lifesaving control method according to claim 14, wherein,
the first gasbag module is arranged at a position of the lifesaving device body corresponding to a chest of the user, and the second gasbag module is arranged at a position of the lifesaving device body corresponding to a back of the user, the control method comprises:
detecting water pressure information after the first gasbag module pops up the lifesaving gasbag;
activating the second gasbag module to pop up the second lifesaving gasbag if the water pressure information meets a second preset condition.

16. A lifesaving control method, applied to a lifesaving device,
wherein, the lifesaving device comprises:
at least one first detection module configured for detecting human body biological characteristic information;
a lifesaving device body capable of being worn on a body of a user; and
at least one first gasbag module arranged on the lifesaving device body, wherein, after being activated, the first gasbag module is capable of popping up a lifesaving gasbag;
the first detection module is in signal connection with the first gasbag module and is configured for activating the first gasbag module when the biological characteristic information detected meets a first preset condition
wherein, the lifesaving control method comprises:
detecting human body biological characteristic information of a user;
activating a first gasbag module to pop up a lifesaving gasbag if the human body biological characteristic information meets a first preset condition,
wherein, after the step of detecting the human body biological characteristic information of the user, and before the step of activating the first gasbag module to pop up the lifesaving gasbag if the human body biological characteristic information meets the first preset condition, the lifesaving control method further comprises:
judging whether abnormal time of human body life characteristic information exceeds a preset threshold or not;
sending a danger prompt to the user if the abnormal time of the human body life characteristic information exceeds the preset threshold, so that the user can manually trigger the first gasbag module.

* * * * *